United States Patent [19]

Portoghese et al.

[11] Patent Number: 4,649,200

[45] Date of Patent: Mar. 10, 1987

[54] SUBSTITUTED PYRROLES WITH OPIOID RECEPTOR ACTIVITY

[75] Inventors: Philip S. Portoghese, Falcon Heights; Andrzej W. Lipkowski, Minneapolis, both of Minn.

[73] Assignee: Regents of the University of Minnesota, Minneapolis, Minn.

[21] Appl. No.: 861,051

[22] Filed: May 8, 1986

[51] Int. Cl.[4] ............................................. C07D 491/22
[52] U.S. Cl. ..................................... 546/26; 548/417; 549/432
[58] Field of Search ........................... 546/26; 548/417

[56] References Cited

PUBLICATIONS

The Condensed Chemical Dictionary, G. G. Hawley, ed., Van Nostrand Reinhold Co., N.Y. (10th ed., 1981) at pp. 90 and 525.
W. R. Martin, Pharmacol. Rev., 35, 283 (1984).
M. Erez et al., J. Med. Chem., 25, 847 (1982).
P. S. Portoghese et al., Life Sciences, 36, 801 (1985).
Rapoport et al, J. A. C. S. 89, 1942(1967).
Astill et al, J. A. C. S. 77, 4079(1955).

Primary Examiner—Donald G. Daus
Assistant Examiner—Cecilia Shen
Attorney, Agent, or Firm—Merchant, Gould, Smith, Edell, Welter & Schmidt

[57] ABSTRACT

Substituted pyrroles of the formula:

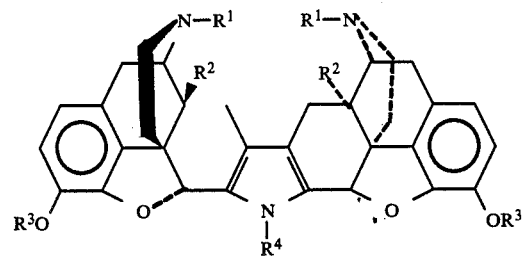

are disclosed wherein $R^1$ is $(C_1-C_5)$alkyl, $C_3-C_6$(cycloalkyl) alkyl, $C_5-C_7$(cycloalkenyl)alkyl, aryl, aralkyl, trans-$(C_4-C_5)$ alkenyl, allyl or furan-2-ylalkyl; $R^2$ is H or OH, $R^3$ is H, $(C_1-C_5)$alkyl or $(C_1-C_5)$alkanoyl and $R^4$ is H or $(C_1-C_5)$ alkyl; as well as the pharmaceutically-acceptable salts thereof. These compounds are useful as analgesics and/or as selective kappa-opioid antagonists.

12 Claims, No Drawings

SUBSTITUTED PYRROLES WITH OPIOID RECEPTOR ACTIVITY

This invention was made with Government support under Grant Number 2RO-1-DA-02659-03A1 awarded by the National Institute on Drug Abuse. The Government has certain rights in this invention.

FIELD OF THE INVENTION

Opium alkaloid derivatives can be coupled to yield bimorphinan compounds comprising a pyrrole ring which exhibit agonist and antagonist activity at opioid receptors.

BACKGROUND OF THE INVENTION

The discovery of multiple receptors for opium alkaloids and their derivatives, or opiates, has attracted considerable interest among research investigators because the physiologic responses mediated by subpopulations of these receptors differ. See W. R. Martin, *Pharmacol. Review*, 35, 283 (1983). Thus, compounds that are highly selective for a single subpopulation of receptors may have clinical utility because undesired pharmacologic effects at other opioid receptor populations would be minimal.

Although selective antagonist compounds are available for mu and delta receptor types, the development of kappa-selective opioid antagonists has been elusive.

In *J. Med. Chem.*, 25, 847 (1982) M. Erez, A. E. Takemori and P. S. Portoghese reported the synthesis of a bivalent compound containing two beta-naltrexamine pharmacophores connected by a oligoethylenoxy spanner. This compound, designated TENA, can be represented by the formula:

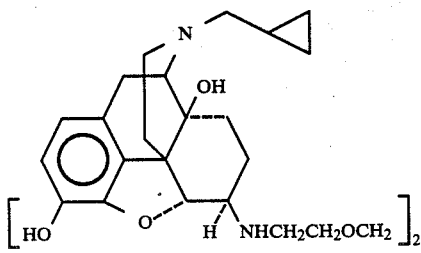

TENA was found to be about 27 times more effective in antagonizing the activity of the kappa receptor agonist, U50488H, relative to the mu receptor agonist, morphine, and it was about five times more effective against the kappa receptor agonist, ethylketazocine, relative to morphine. See P. S. Portoghese et al., *Life Sciences*, 36, 801 (1985).

However, due to the implication of the kappa opioid receptor in the mediation of important physiological responses such as appetite and traumatic paralysis, a need exists for compounds which can more selectively block kappa opioid receptor sites.

BRIEF DESCRIPTION OF THE INVENTION

The present invention is directly to biologically-active compounds comprising a substituted pyrrole of the formula III:

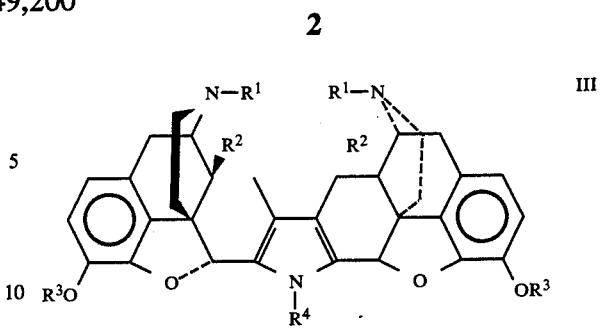

wherein $R^1$ is $(C_1-C_5)$alkyl, $C_3-C_6$(cycloalkyl)alkyl, $C_5-C_7$ (cycloalkenyl)alkyl, aryl, aralkyl, trans-$(C_4-C_5)$alkenyl, allyl, or (furan-2-yl)alkyl; $R^2$ is H or OH, $R^3$ is H, $(C_1-C_5)$ alkyl or $(C_1-C_5)$alkanoyl and $R^4$ is H or $(C_1-C_5)$alkyl; and the pharmaceutically-acceptable salts thereof.

The alkyl moiety present in the $R^1$ group which links the cycloalkyl, cycloalkenyl, aryl, or furan-2-yl moiety to the basic nitrogen atom is a lower(alkyl) group, preferably $-(CH_2)_n-$, wherein n is about 1-5; most preferably n is 1, e.g., $R^1$ is $C_3-C_6$(cycloalkyl)methyl, $C_5-C_7$-(cycloalkenyl)methyl, arylmethyl or furan-2-ylmethyl. Preferred aryl moieties include phenyl, benzyl, tolyl, xylyl, anisyl and the like.

The compounds of the present invention are derived by coupling two opiate molecules, each of which includes a $C_6$-keto group, by means of certain amino compounds, to yield a substituted pyrrole ring. Thus, the present compounds are formally derivatives of 6,6'-imino[7,7'-bimorphinan]. In compound III, a bond designated by a broken line indicates one projecting or positioned below the plane of the phenyl rings, whereas a bond designated by a wedged or darkened line indicates one extending above the plane of the phenyl rings.

All of the pyrrole compounds of the present invention wherein $R^1=CH_3$ exhibit some degree of agonist activity with respect to opioid receptors such as mu receptors, and would therefore be expected to possess utility as analgesics, soporifices, antidiarrhea agents and the like. However, the preferred compounds of the present invention also exhibit the ability to block kappa-opioid receptors with minimal blockage at mu and delta opioid receptors. These kappa-opioid antagonists include compounds of the formula III wherein $R^1$ is $C_3-C_6$(cycloalkyl)alkyl or $C_5-C_7$(cycloalkenyl) alkyl, preferably wherein $R^1$ is $C_3-C_6$(cycloalkyl)methyl, and most preferably wherein $R^1$ is cyclopropylmethyl. $R^4$ can be H or $(C_1-C_5)$alkyl, preferably H, methyl or ethyl; $R^2$ can be H or OH, preferably H, and $R^3$ is H, $(C_1-C_5)$alkyl or $(C_1-C_5)$ alkanoyl, and preferably is H, methyl or acetyl. For example, in one assay, pyrrole III where $R^1$ is cyclopropylmethyl, $R^2$ is OH, $R^3$ is H and $R^4$ is methyl is at least 30 times more selective than TENA as a kappa-opioid receptor antagonist.

Therefore, the present invention is also directed to a method for blocking kappa-opioid receptors in mammalian tissue comprising contacting said receptors with an effective amount of one of the present kappa-opioid antagonists of formula III. These antagonists can be used as pharmacologic and biochemical probes of opioid receptor structure and function, and may also be useful clinically as appetite suppressants or to block the bodily paralysis caused by endogenous kappa receptor agonists that are released as a result of spinal trauma. For example, see J. E. Morely et al., *Eur. J. Pharmacol.*, 112, 17 (1985) and A. I. Faden et al., *Reg. Peptides*, 11, 35 (1985).

DETAILED DESCRIPTION OF THE INVENTION

The syntheses of representative compounds of formula III from starting materials of formula I is outlined on Table I.

protected, can be prepared from compounds Ia-g. These intermediates can be N-alkylated and deprotected to yield compounds of formula I wherein $R^1$ is $C_2$–$C_5$(alkyl), $C_4$–$C_6$(cycloalkyl)alkyl, $C_5$–$C_7$ (cycloalkenyl)alkyl, aryl, aralkyl, trans-$C_4$–$C_5$-alkenyl or furan-2-ylalkyl, by the application of well-known reactions.

For example, the free hydroxyl groups of compounds

TABLE I

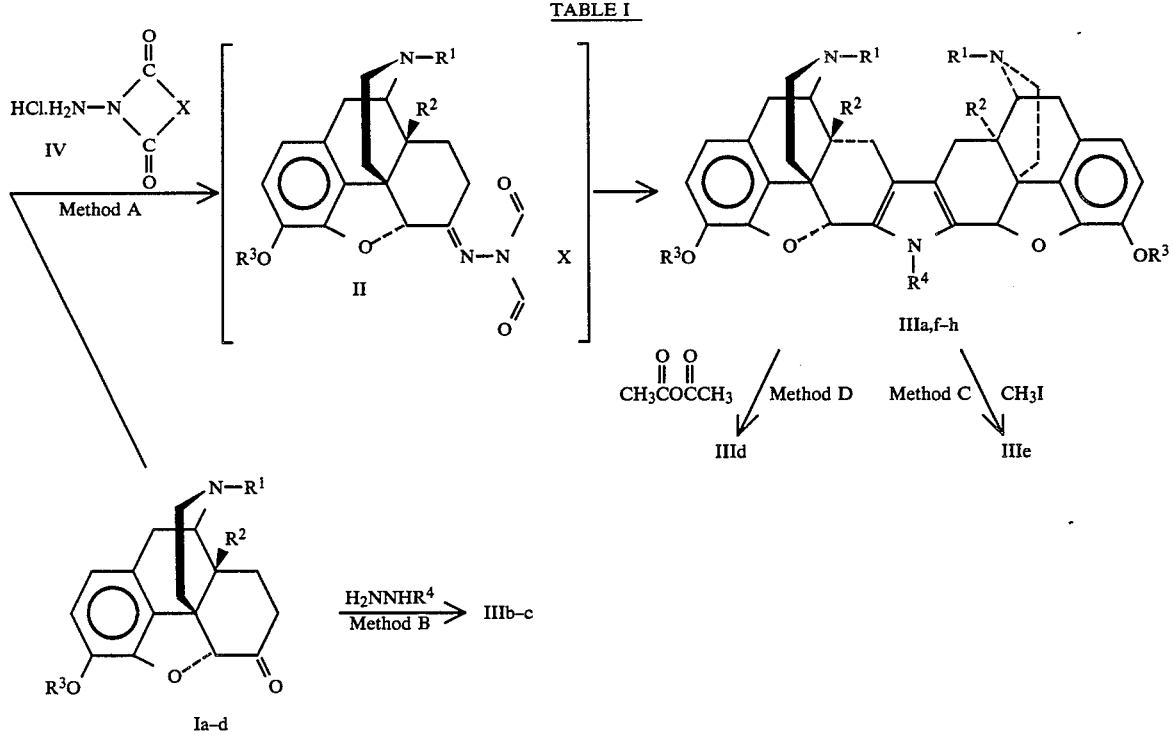

The structures, common names and Merck Index reference numbers of representative starting materials of formula I are summarized on Table II.

TABLE II

| Compound | $R^1$ | $R^2$ | $R^3$ | Common Name | Merck No.[2] |
|---|---|---|---|---|---|
| Ia | CH$_2$CH(CH$_2$)$_2$ | OH | H | naltrexone | 6209 |
| Ib | CH$_3$ | OH | H | oxymorphone | 6837 |
| Ic | CH$_3$ | H | H | hydromorphone | 4714 |
| Id | CH$_3$ | H | CH$_3$ | hydrocodone | 4687 |
| Ie[1] | CH$_2$CH(CH$_2$)$_2$ | H | H | — | |
| If | CH$_2$CH=CH$_2$ | OH | H | naloxone | 6208 |
| Ig | CH$_3$ | OH | CH$_3$ | oxycodone | 6827 |

[1]Preparation: M. Gates et al., *J. Med. Chem.*, 7, 127 (1964).
[2]The Merck Index, W. Windholz, ed., Merck & Co., Rahway, NJ (10th ed. 1983).

Other starting materials of formula I can be prepared by synthetic methods which are well-known in the art of organic chemistry. For example, compounds of formula I wherein $R^1$ is H and $R^3$ is a suitable protecting group, and wherein the 6-keto group has also been of formula I, e.g., $R^2$=OH and/or $R^3$=H, can be protected by acid-labile groups such as tetrahydropyran-1-yl, trimethylsilyl, 1-methoxy-isopropyl and the like as disclosed in *Compendium of Organic Synthetic Methods*, I. T. Harrison et al., eds., Wiley-Interscience, New York, NY (1971) at pages 124–131, (hereinafter "*Compedium*") the disclosure of which is incorporated by reference herein. The protection of the 6-keto group of compounds of formula I by its reversible conversion into a ketal or a thioketal group are disclosed in *Compedium*, at pages 449–453, the disclosure of which is incorporated by reference herein. Methods for the demethylation of N-methyl amines have been disclosed, for example, in *Compendium* at page 247, *J. Amer. Chem. Soc.*, 89, 1942 (1967) and *J. Amer. Chem. Soc.*, 77, 4079 (1955), the disclosures of which are incorporated by reference herein.

Procedures for the alkylation of secondary amines with halides under basic or neutral conditions are well-known. For example, see *Compendium* at pages 242–245; *Org. Synth.*, 43, 45 (1963); *J. Org. Chem.*, 27, 3639 (1962) and *J. Amer. Chem. Soc.*, 82, 6163 (1960), the disclosures of which are incorporated by reference herein.

Compounds of formula III can be prepared by two different procedures. In method A, a hydrochloride or other acid salt of a compound of formula I is treated with the acid salt of an N-aminoimide or with a hydrazide that cyclizes to an aminoimide under the reaction conditions. Typically, a one molar excess of the hydrochloride of an N-aminoimide IV or a hydrazide is mixed with the opiate hydrochloride I in an organic solvent such as dimethylformamide (DMF) with agitation and heating, as necessary, to yield compound III. Compound III can be purified as the acid salt by column gel filtration chromatography.

N-Aminoimides useful in method A include those of formula IV, wherein X is alkylene, alkylidenyl, o-phenylene and the like. Preferred N-aminoimides include N-aminosuccinimide hydrochloride, N-aminomaleimide.HCl, N-aminoglutarimide.HCl, and N-aminophthalimide.HCl. The preparation of N-aminosuccinimide.HCl is disclosed by J. G. Krause et al., in *J. Org. Chem.*, 37, 2040 (1972), the disclosure of which is incorporated by reference herein. Useful hydrazides for use in method A include succinylhydrazide monoethyl ester.

In the course of the conversion of I to III, it is believed that the reactive, transient imide hydrazone intermediate II is formed. Two molecules of II then undergo coupling through C-7, followed by cyclization to yield pyrrole III.

Compounds of formula III can also be prepared by method B, which is a variation of Piloty-Robinson synthesis. See N. F. Sidgwick, *Organic Chemistry of Nitrogen Compounds*, Oxford (3rd ed. 1966) at pages 619–641. The hydrochlorides of compounds of formula I are reacted with the hydrochloride salt of hydrazine or a monoalkylhydrazine [$H_2NNHR^4$ wherein $R^4=(C_1-C_5)$ alkyl] to directly yield compounds of formula III, wherein $R^4=H$ or $(C_1-C_5)$alkyl, respectively, via the corresponding azine (not depicted). For example, a compound of formula III can be formed by reacting the hydrochloride salt of I in a mixture of DMF and acetic acid with 50-mole % of hydrazine.2HCl or a monoalkylhydrazone.2HCl for about 7.5–15 hrs at 100°–150° C.

The diacid salts such as the dihydrochlorides of formula III, wherein either of $R^3=H$ can be converted into the corresponding $(C_1-C_5)$alkanoyloxy derivatives [$R^3=(C_1-C_5)$alkylC=O] by dissolving the starting material in DMF and adding the appropriate $(C_1-C_5)$alkyl anhydride thereto. After a suitable reaction time, e.g., 10–18 hrs at 18°–25° C., the product can be precipitated from the reaction mixture and purified by recrystallization.

The diacid salts such as the dihydrochlorides of formula III, wherein either of $R^3=H$ can be converted into the corresponding $(C_1-C_5)$alkoxy derivatives [$R^3=(C_1-C_5)$alkyl] by dissolving the starting material in DMF and adding an excess of the appropriate $(C_1-C_5)$alkyl iodide and an amine such as diisopropylethylamine. The reaction can be conducted at an elevated temperature for about 4–10 hrs. The final dihydrochloride product can be purified by column chromatography.

Although only the use of a single starting material of formula I in method A or method B to yield compounds of formula III which are symmetrical with respect to $R^1$, $R^2$ and $R^3$ is exemplified herein, it is also possible to prepare compounds of formula III which are unsymmetrical with respect to these substituents. For example, employing a mixture of Ia and Ie in method A would be expected to afford a certain proportion of compound III wherein the $R^1$ group on the alpha-nitrogen atom and the beta-nitrogen atom are not both $CH_3$ or both cyclopropylmethyl, but rather, wherein one $R^1$ is $CH_3$ and the other $R^1$ is cyclopropylmethyl. Since the resultant three component mixtures can be resolved by chromatographic techniques, such compounds are also intended to fall within the scope of the present invention and the appended claims. For example, in such compounds $R^1$, $R^2$ and $R^3$ are individually the substituents recited therefore.

Unsymmetrical compounds of formula III with respect to $R^3$ can also be prepared by the partial protection of a compound of formula III wherein both $R^3$ and H, followed by the reaction of the free OH group with an anhydride or an alkyl halide. Deprotection affords a compound of formula III having one free phenolic hydroxyl group, which hydroxyl group can be alkylated or esterified as described hereinabove.

The invention also comprises the pharmaceutically-acceptable salts of the biologically-active compounds of formula III together with a pharmaceutically-acceptable carrier for administration in effective, non-toxic dose form. Pharmaceutically-acceptable amine salts may be salts of organic acids, such as acetic, lactic, malic, tartaric or p-toluene sulphonic acid, and the like as well as salts of pharmaceutically-acceptable mineral acids such as phosphoric, hydrochloric or sulfuric acid, and the like.

These physiologically-acceptable salts are prepared by methods known in the art, e.g., by dissolving the free pyrrole compound with an excess of the acid in aqueous alcohol.

In clinical practice, the formula III pyrroles or the salts thereof will normally be administered orally or parenterally, by injection or infusion, in the form of a pharmaceutical preparation comprising the active ingredient in combination with a pharmaceutically-acceptable carrier which may be a solid, semi-solid or liquid diluent or an ingestible capsule. The compound or its salt may also be used without carrier material. As examples of pharmaceutical preparations may be mentioned tablets, suspensions, liposomes, and the like. Usually the active substance will comprise between about 0.05 and 99%, or between 0.1 and 95% by weight of the preparation, for example, between about 0.5 and 20% of preparation intended for injection and between about 0.1 and 50% of preparations intended for oral administration.

The invention will be further described by reference to the following detailed examples.

EXAMPLE I

Method A

The opiate hydrochlorides Ia-d (1 mmol) and N-aminosuccinimide hydrochloride (2 mmol) were heated in 3 ml of dimethylformamide (DMF) on a steam bath for 1.5 hours with vigorous stirring. The reaction mixture was cooled to 20° C. and was diluted with 50 ml of 10% aqueous sodium bicarbonate ($NaHCO_3$). The precipitated crude product was extracted 3 times with ethyl acetate (50 ml), and the extracts were pooled and evaporated to dryness. The residue was dissolved in 1 ml of methanol, treated with conc. aqueous HCl (0.3 ml), and the solution was purified by gel filtration column chromatography on Sephadex LH-20 in 90% methanol. After evaporation of methanol, the product was dried in vacuo at 25° C. over sodium hydroxide to yield the dihydrochloride salts of IIIa, IIIh, IIIf and IIIg, respectively.

EXAMPLE II

Method B

A 2 ml mixture of glacial acetic acid and DMF (1:1) containing the opiate hydrochlorides (Ia-d) (1 mmol) and hydrazine dihydrochloride, methyl hydrazine dihydrochloride or ethyl hydrazine dihydrochloride (0.5 mmol) was stirred for 10 hours at 130° C. Toluenesulfonic acid was added to ensure the solubility of the azine intermediate. After cooling, the mixture was diluted with diethyl ether (25 ml), and the precipitate was collected by filtration. The precipitate was dissolved in water (5 ml), 10% aqueous NaHCO$_3$ (10 ml) was added, and the precipitated product was extracted with ethyl acetate and purified by chromatography as described in Example I. The reaction of Ia-d with hydrazine.2HCl by this procedure afforded the dihydrochloride salts of IIIa, IIIh, IIIf and IIIg, respectively. The reaction of Ia with methylhydrazine.2HCL yielded IIIh, and the reaction of Ia with ethylhydrazine.2HCl yielded IIIc.

EXAMPLE III

Method C

The bimorphinan dihydrochloride (IIIa) (0.2 mmol) was dissolved in DMF (0.5 ml), and acetic anhydride was added slowly with stirring, and the mixture was stirred for 12 hours at 20° C. The product (IIId) was precipitated from the reaction mixture by addition of ethyl acetate (4 ml). The diacetate product was crystallized from isopropanol-DMF.

EXAMPLE IV

Method D

The bimorphinan dihydrochloride (IIIa) (0.1 mmol) was dissolved in DMF (0.5 ml), and methyl iodide (0.25 mmol) and diisopropylethylamine (0.6 mmol) were added. After stirring the mixture at 90° C. for 6 hours, it was diluted with 10% aqueous ammonium hydroxide (NH$_4$OH) (10 ml) and extracted with ethyl acetate (3×10 ml). The pooled extracts were washed 3 times with 10% NH$_4$OH (10 ml) and then with water. After removal of the solvent, the residue was dissolved in methanol (0.5 ml) containing 0.1 ml of HCl and chromatographed in Sephadex LB-20 (Sigma Chemical Co., St. Louis, MO) in methanol to yield IIIe.

The structure and physical characterization data of pyrroles IIIa–IIIh is summarized on Tables III and IV, below.

TABLE III

Characterization of Pyrrole Derivatives III.

| Compound | R$^1$ | R$^2$ | R$^3$ | R$^4$ | Yield | R$_f^1$ A | R$_f^1$ B | R$_f^2$ min. | [α]$^3$ |
|---|---|---|---|---|---|---|---|---|---|
| IIIa | CH$_2$CH(CH$_2$)$_2$ | OH | H | H | 90%[4], 75%[5] | 0.46 | 0.36 | 6.86 | −377 |
| IIIb | CH$_2$CH(CH$_2$)$_2$ | OH | H | CH$_3$ | 62%[5] | 0.48 | 0.40 | 6.91 | −330 |
| IIIc | CH$_2$CH(CH$_2$)$_2$ | OH | H | C$_2$H$_5$ | 32%[5] | 0.47 | 0.38 | 6.94 | −305 |
| IIId | CH$_2$CH(CH$_2$)$_2$ | OH | CH$_3$CO | H | 84%[6] | 0.47 | 0.40 | 6.95 | −373 |
| IIIe | CH$_2$CH(CH$_2$)$_2$ | OH | CH$_3$ | H | 75%[7] | 0.46 | 0.94 | 11.60 | — |
| IIIf | CH$_3$ | H | H | H | 58%[4] | 0.29 | 0.18 | 7.72 | −366 |
| IIIg | CH$_3$ | H | CH$_3$ | H | 48%[4] | 0.27 | 0.43 | 19.00 | −333 |
| IIIh | CH$_3$ | OH | H | H | 90%[4] | 0.25 | 0.21 | 6.22 | −377 |

[1]Silica gel GF (0.25 mm thick) TLC plates using solvent system A (n-BuOH—HOAc—H$_2$O, 2:1:1) or B (CHCl$_3$—MeOH—NH$_4$OH, 18:2:1).
[2]Retention time on a reverse phase C-8 (5 u) column (0.46 × 25 cm) at a flow rate of 1 ml/min [MeOH—TFA (0.1%), 6:4].
[3][α]$_D^{23}$ (Cl, MeOH) of the dihydrochloride salts, mp >280° C.
[4]Procedure A;
[5]Procedure B;
[6]Procedure C;
[7]Procedure D.

TABLE IV $^{13}$C Chemical Shifts of Pyrrole Derivatives III.

| Carbon No. | IIIa | IIIb | IIIc | IIIf | IIIg | IIIh |
|---|---|---|---|---|---|---|
| 1 | 121.34 | 118.57 | 119.54 | 121.97 | 120.38 | 118.64 |
| 2 | 113.79 | 117.89 | 118.83 | 115.21 | 119.15 | 117.73 |
| 3 | 140.44 | 140.50 | 141.40 | 140.30 | 142.45 | 140.46 |
| 4 | 143.41 | 143.23 | 144.49 | 143.54 | 144.24 | 143.40 |
| 5 | 83.24 | 83.31 | 84.26 | 83.70 | 90.07 | 83.22 |
| 6 | 118.52 | 121.37 | 122.38 | 118.92 | 115.25 | 121.43 |
| 7 | 117.78 | 113.89 | 114.82 | 117.51 | 115.19 | 113.73 |
| 8 | 28.17 | 28.27 | 29.21 | 25.54 | 25.55 | 28.31 |
| 9 | 61.19 | 61.26 | 62.35 | 59.96 | 60.18 | 65.50 |
| 10 | 23.53 | 23.66 | 24.51 | 32.89 | 32.12 | 28.90 |
| 11 | 124.74 | 124.77 | 125.81 | 125.29 | 125.91 | 124.73 |
| 12 | 129.19 | 129.24 | 130.22 | 127.05 | 127.07 | 129.13 |
| 13 | 46.02 | 46.07 | 47.06 | 46.47 | 44.55 | 46.43 |
| 14 | 72.13 | 72.20 | 73.14 | 38.44 | 38.03 | 72.28 |
| 15 | 29.00 | 29.04 | 30.51 | 38.39 | 35.90 | 38.67 |
| 16 | 45.63 | 45.81 | 46.63 | 41.47 | 41.43 | 45.40 |
| 18 | 56.74 | 56.85 | 57.83 | 40.52 | 55.69 | 41.04 |
| 19 | 5.71 | 5.79 | 6.63 | | | |
| 20 | 5.04 | 5.31 | 5.96 | | | |
| 21 | 2.71 | 2.93 | 3.68 | | | |
| R$^4$ | | 25.52 | 38.60 | | | |
| | | | 28.33 | | | |
| R$^3$ | | | | | | 56.39 |

[a]Determined on the dihydrochloride salts in DMSO—d$_6$.
[b]Since the compounds exhibit C$_2$ symmetry, the chemical shift values of equivalent carbons in each half of the molecule are identical.

EXAMPLE V

Evaluation of Agonist and Antagonist Activity

A. Materials and Methods

1. Guinea Pig Ileal Longitudinal Muscle (GPI).

Ilea from guinea pigs were taken approximately 10 cm from the ileocaecal junction, and a strip of longitudinal muscle with the myenteric plexus attached was prepared by method of Rang et al., *Brit. J. Phamacol.*, 22, 356 (1964), the disclosure of which is incorporated by reference herein. A 1 cm portion of this strip was then mounted between two platinum electrodes placed in a 10 ml organ bath and connected to an isometric transducer; contractions were recorded on a polygraph. Contractions of the ileal strip were initiated by supra-maximal rectangular pulses in all preparations (80 V of 0.5 ms duration at a frequency of 0.1 Hz). Krebs bicarbonate solution containing 1.25 uM chlorpheniramine maleate was the bathing solution and was continuously bubbled with 95% $O_2$ and 5% $CO_2$. The organ bath was maintained at 36°–37° C. The longitudinal muscle strip was allowed to equilibrate with continuous stimulation for a minimun of 90 min. Cumulative concentration-response curves were determined after drugs were added to the bath in 10- to 50-uL amounts and washed out with two 10 ml portions of buffer after noting their maximum effects.

2. Mouse Vas Deferens (MVD)

This assay was performed according to the description by Henderson et al., *Brit. J. Pharmacol.*, 46, 764 (1972), the disclosure of which is incorporated by reference herein. Both vasa deferentia were dissected out of mice and mounted singly through two platinum ring electrodes in a 10 ml organ bath. The bath contained Krebs bicarbonate solution that was continuously bubbled with 95% $O_2$ and 5% $CO_2$. The organ bath was maintained at 37° C. The tissue was attached to an isometric transducer and stimulated transmurally with rectangular pulses (0.1 Mz, 1 ms duration, supramaximal voltage). Drugs were added cumulatively to the bath in 10 to 50 ul amounts and washed out after noting their maximum effect.

B. Pharmacology

Compounds IIIa–IIIh and TENA were tested on the electrically-stimulated guniea pig ileal longitudinal muscle (GPI) and, where appropriate, the mouse vas deferens preparation (MVD). The results of this evaluation are summarized on Table V, below.

and U50488H, in the GPI. This was manifested by displacement of the EK concentration-response curve to higher concentration by factors of up to about 140 ($IC_{50}$ ratio) in the presence of 20 nM of the compounds. When the selective kappa agonist (U50488H) was employed, higher $IC_{50}$ ratio values were observed for compound IIIa. These results contrast with the observation that compounds IIIa–IIId are considerably less effective in antagonizing the effect of morphine (a mu receptor-selective agonist). In this connection, it can be seen that the morphine $IC_{50}$ ratios at the same concentration of antagonist (20 nM) are not greater than one-tenth of those $IC_{50}$ ratios obtained with EK. Thus, compounds IIIa–IIId are highly selective kappa-opioid receptor antagonists. Compounds IIIa–IIId are all more selective than the most potent known kappa-opioid antagonist, TENA. Of these compounds, it appears that IIIb possesses the greatest kappa selectivity, as no significant antagonism of morphine was observed at 20 nM. Also it is noteworthy that the ability of these compounds to antagonize [D-Ala$^2$,D-Leu$^5$]enkephalin (a selective delta opioid receptor agonist) in the MVD is relatively weak, with $IC_{50}$ ratios not greater than 0.04 of those of EK in the GPI.

All of the members of the N-methyl series (IIIf-h) act as full opioid agonists in the GPI. Their agonist potencies range from 3–0.2 times that of morphine. In the GPI that was depleted of functional mu receptors with β-FNA by the method of S. J. Ward et al., *Eur. J. Pharmacol.*, 85, 163 (1982), the $IC_{50}$ of IIIh was increased by a factor of 11. None of the members in this series exhibited antagonistic activity at mu or kappa-opioid receptors.

The most selective antagonist IIIb was tested in vivo using the mouse writhing procedure of G. Hayashi et al., *Eur. J. Pharmacol.*, 16, 63 (1971). It is believed that this response is mediated by kappa receptors. Mice were treated with 50 nmol of the agonist (morphine, EK, or U50488H) subcutaneously and the antagonist was administered intracerebroventricularly (ICV). The $ED_{50}$ ratios [(agonist+IIIb)/agonist control] for morphine, EK, and U50488H were 0.85, 3.85, and 15.71, respectively. Therefore, the observed inhibition exhibited by

TABLE V

Activities of Pyrrole Derivatives III on the GPI and MVD Preparations

| Compound No. | GPI Agonism[a] | Conc. (nM) | GPI $IC_{50}$ Ratio[b] Morphine Sulfate | Ethylketazocine[f] | U50488H[c] | MVD Agonism[a] | MVD $IC_{50}$ Ratio[b] DADLE[d] |
|---|---|---|---|---|---|---|---|
| IIIa | 14% @ 200 nM | 2 | 0.92 ± 0.16 | 8.8 ± 0.13 | 11.0 ± 1.1 | | |
| | | 20 | 4.7 ± 0.8 | 49.7 ± 15.6 | 178 ± 18 | 16% @ 1 uM | 2.0 ± 0.1 |
| IIIb | 0 @ 1 uM | 20 | 1.2 ± 0.3 | 165 ± 30 | | 42% @ 1 uM | 4.5 ± 0.7 |
| IIIc | 0 @ 1 uM | 2 | — | — | | | 1.8 ± 0.3 |
| | | 20 | 2.2 ± 0.7 | 147 ± 20 | | 41% @ 1 uM | 4.2 ± 1.1 |
| IIId | 32% @ 1 uM | 20 | 8.0 (2) | 697 (2) | | 32% @ 1 uM | 3.5 ± 1.3 |
| IIIe | 0 @ 1 uM | 20 | 0.8 (2) | 4 (2) | | 39% @ 1 uM | 0.6 ± 0.1 |
| IIIf | 3.1 ± 0.4 | 10 | 0.3 ± 0.1 | 0.5 ± 0.04 | | | |
| IIIg | 0.2 ± 0.04 | 100 | 0.5 ± 0.07 | 0.4 ± 0.07 | | | |
| IIIh | 0.23 ± 0.05 | 50 | 0.9 ± 0.2 | 0.4 ± 0.05 | | | |
| TENA[e] | 10% @ 10 nM | 20 | 4.20 ± 1.20 | 19.6 ± 2.40 | | 32% @ 0.1 uM | 1.2 ± 0.2 |

[a] For ligands that are partial or pure antagonists, the highest concentration and maximal response is given. Potencies of pure agonists (IIIe-h) are relative to morphine = 1.
[b] $IC_{50}$ of agonist in prescence of antagonist divided by control $IC_{50}$ in the same preparation.
[c] 1-(3', 4'-dichlorophenyl-N—methyl-acetamido)-trans-2-prrolidinohexane; J. Szmuszkovicz and P. F. von Voigtlander, J. Med. Chem. 25, 1125 (1982).
[d] [D-Ala$^2$, D-Leu$^5$]enkephalin(Calbiochem).
[e] M. Erez et al., J. Med. Chem., 25, 847 (1982) (synthesis).
[f] Sterling-Wintrop Research Institute, Renesselear, NY.

Compounds in the N-cyclopropylmethyl series (IIIa–IIIe) possessed little or no agonistic activity in either of the preparations. However, compounds IIIa-IIe exhibited a high antagonistic potency toward the kappa opioid receptor agonists, ethylketazocine (EK) IIIb of the writhing inhibition of morphine, EK or U50488H in the whole animal model correlates with that observed in vitro.

C. Discussion

The N-cyclopropylmethyl compounds IIIa–e display a unique pharmacologic profile in that they exhibit substantially greater antagonist potency at kappa-opioid receptors than at mu or delta opioid receptors. This is in contrast to the activity of the well-known opioid antagonists such as naloxone or naltrexone, which possesses much greater potency at mu receptors. Moreover, IIIa–d are more selective than the selective kappa antagonist, TENA, by at least a factor of ten. The in vivo antagonist selectivity parallels that observed in the GPI preparation. Because IIIb displays no agonist effect in the GPI or MVD, it can be regarded as a "pure" kappa-opioid receptor antagonist. Therefore, compound IIIb and the other compounds of the present invention which exhibit kappa receptor antagonist activity should be useful for pharmacological studies of opioid receptor activity and function and may be therapeutically useful in conditions where selective blockage of kappa receptors is desired. This includes blockage of the appetite response, blockage of paralysis due to spinal trauma, and a variety of other physiologic activities that may be mediated through kappa receptors.

Of interest is the relationship between compounds IIIa–d and TENA. Since IIIa–d are considerably more kappa-selective and more potent than TENA, it is possible that the geometric orientation of the two pharmacophores, with respect to each other, contributes to this enhancement. Since the x-ray crystal structure of IIIa indicates that it possesses a two-fold axis of symmetry at the juncture of the pyrrole ring, TENA may interact with receptors with its opiate pharmacophores in a similar orientation. In view of the conformational mobility of the spacer in TENA, its pharmacophores can assume a similar orientation as those in IIIa–d but only with selected rotamers of the spacer.

Although the N-methylated compounds IIIf–h did not exhibit significant kappa receptor antagonism, these compounds and other compounds of formula III wherein $R^1$ is $(C_1-C_5)$alkyl would be expected to exhibit analgesic activity due to their agonist behavior.

The invention has been described with reference to various specific and preferred embodiments and techniques. However, it should be understood that many variations and modifications may be made while remaining within the spirit and scope of the invention.

What is claimed is:

1. A composition of matter comprising a substituted pyrrole of the formula:

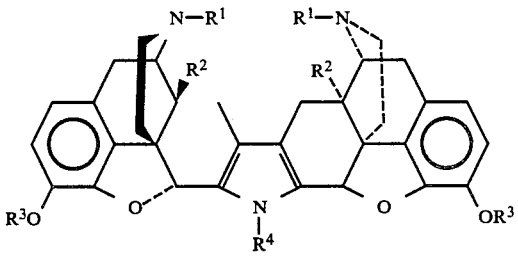

wherein $R^1$ is $(C_1-C_5)$ alkyl, $C_3-C_6$(cycloalkyl)alkyl, $C_5-C_7$ (cycloalkenyl)alkyl, aryl, aralkyl, trans-$(C_4-C_5)$alkenyl, allyl or furan-2-ylalkyl; $R^2$ is H or OH, $R^3$ is H, $(C_1-C_5)$ alkyl or $(C_1-C_5)$alkanoyl and $R^4$ is H or $(C_1-C_5)$ alkyl; and the pharmaceutically-acceptable salts thereof.

2. The composition of claim 1 wherein $R^1$ is $C_3-C_6$(cycloalkyl)alkyl or $C_5-C_7$(cycloalkenyl)alkyl.

3. The composition of claim 1 wherein $R^2$ is H or OH.

4. The composition of claim 1 wherein $R^4$ is H or $(C_1-C_5)$alkyl.

5. A composition of matter comprising a substituted pyrrole of the formula:

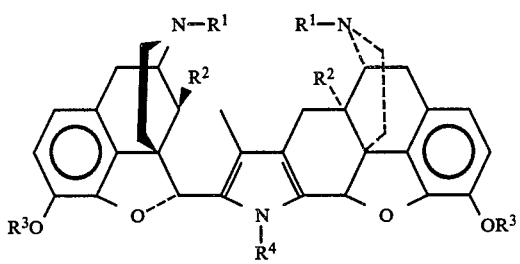

wherein $R^1$ is $C_3-C_6$(cycloalkyl)alkyl or allyl, $R^2$ is H or OH, $R^4$ is H or $(C_1-C_5)$alkyl and $R^3$ is H, $(C_1-C_5)$alkyl or $(C_1-C_5)$alkanoyl; and the pharmaceutically-acceptable salts thereof.

6. The composition of claim 5 wherein $R^1$ is cyclopropylmethyl.

7. The composition of claim 5 wherein $R^4$ is H, methyl or ethyl.

8. The composition of claim 5 wherein $R^3$ is H, methyl or acetyl.

9. The composition of claim 10 wherein $R^4$ is H, methyl or ethyl, $R^2$ is OH and $R^3$ is H.

10. The composition of claim 5 wherein $R^1$ is allyl.

11. The composition of claim 6 wherein $R^2$ and $R^3$ are H.

12. A method for blocking kappa-opioid receptors in mammalian tissue comprising contacting said receptors with an effective amount of the compound of claim 5.

* * * * *